US005478329A

United States Patent [19]
Ternamian

[11] Patent Number: 5,478,329
[45] Date of Patent: Dec. 26, 1995

[54] TROCARLESS ROTATIONAL ENTRY CANNULA

[76] Inventor: Artin M. Ternamian, 401-2425 Bloor Street, W. Toronto, Ontario, Canada, M6S 4W4

[21] Appl. No.: 239,368

[22] Filed: May 6, 1994

[51] Int. Cl.$^6$ .................................................. A61M 5/32
[52] U.S. Cl. ............................ 604/274; 604/264; 604/158
[58] Field of Search ............................ 604/93, 104, 108, 604/109, 158, 164, 188, 264, 268, 270, 272, 274

[56] References Cited

U.S. PATENT DOCUMENTS

| | | | |
|---|---|---|---|
| 4,935,025 | 6/1990 | Bundy et al. | 606/180 |
| 5,147,376 | 9/1992 | Ranetti | 606/170 |
| 5,258,003 | 11/1993 | Ciaglia et al. | 606/185 |
| 5,271,380 | 12/1993 | Riek et al. | 128/4 |
| 5,364,372 | 11/1994 | Danks et al. | 604/264 |

OTHER PUBLICATIONS

Brochure by Boss Instruments, Ltd. for "Fine Instrumentation for the Art of Endoscopic Surgery".
Brochure by Karl Storz for Trocars, size 5.5 mm, Double puncture approach.
Brochure by Dexide Inc. for Trocar.
Brochure by Cook Surgical for Laparoscopic Introducer Set (1991).
Brochure by Core Dynamics, Inc. for "Entree Disposable Trocar and Reusable Automatic Valve Cannula".
Brochure for Cook Inc. for Laparoscopic Introducer Set.
Marrs, R. P., Brochure for "Laparoscopic Access Sheath Sets".
Topel, H. C., Brochure for "Endoscopic Introducer/Extractor".
Brochure for Origin Medsystems Canada, Single Use Blunt Tip Trocar.
Brochure by Ethicon Endo–Surgery for Endoscopic Products Trocars & Accessories, Endopath Radiolucent Trocars Single Patient Use (1994).
Brochure for Snowden Pencer "Endo–Value Trocar/Cannula System" (Nov. 1992).
Laparoscopic Gynecologic Surgery "Preparing for the Unexpected: Abdominal Adhesions": Full Scope–Endopath Tristar.
Laparoscopic Surgery Micro–France, Trocars.
Brochure by Circon Acmi, Laparoscopy and Thoracoscopy Instrumentation Complete Instrumentation System.
Karl Storz—Endoskope Spare Part List for Laparoscopes–Pelviscopes (pp. GYN–SP 15–18).
The Journal of the American Association of Gynecologic Laparoscopists, vol. 1, No. 2, Feb. 1994, "The New Sensor–Equipped Veress Needle" by Thomas I. Janicki, M.D. (pp. 154–156).
Brochure by Origin for "Gaseless Laparoscopy With Mechanical Peritoneal Distention".
Steven G. Kaali, M.D. "Introduction of the Opti–Trocar", The Journal of the American Assoc. of Gynecologic Laparoscopists, vol. 1, No. 1, pp. 50–54, Nov. 1, (1993).
Jamie S. Vasquez, M.D. et al, "Vascular Complications of Laparoscopic Surgery", The Journal of the American Assoc. of Gynecologic Laparoscopists, vol. 1, No. 2, pp. 163–167, Feb. (1994).

(List continued on next page.)

Primary Examiner—Corrine M. Maglione
Assistant Examiner—Michael L. Arness
Attorney, Agent, or Firm—Brumbaugh, Graves, Donohue & Raymond

[57] ABSTRACT

A cannula for safely and easily gaining access to a body cavity without the use of a trocar, has screw threads on its outer surface and a lumen within the cannula extending throughout the entire length of the cannula. The distal end of the cannula is shaped, along its periphery, to penetrate and/or cut tissue layers of the body wall to gain access to a body cavity. The lumen is sufficiently large throughout its length to allow passage of instruments from the proximal end of the cannula directly into the body cavity, once the cannula has been inserted. A method for gaining access to a body cavity with the cannula is also described.

20 Claims, 10 Drawing Sheets

OTHER PUBLICATIONS

John W. Byron, et al., "A Randomized Comparison of Verres Needle and Direct Trocar Insertion for Laparoscopy", Obstetrical and Gynecological Survey, vol. 49, No. 2, pp. 181–182, (1993).

Querleu D. et al., "Complications of gynecologic laparoscopic surgery—A French multicenter collaborative study", NEJM, pp. 220, (1993).

Jeffrey H. Peters, M.D. et al., "Complications of laparoscopic cholecystectomy", Surgery, vol. 110, pp. 769–778, Oct. (1991).

D. Enrique Lehmann–Willenbrock et al., "Pelviscopy/Laparoscopy and its Complications in Germany, 1949–1988", The Journal of Reproductive Medicine, Chapter 43, pp. 285–291.

Steven G. Kaali, M.D. et al., "Incidence of Bowel Injury Due to Dense Adhesions at the Sight of Direct Trocar Insertion", The Journal of Reproductive Medicine, Chapter 26, p. 167.

Marvin J. Wexler, M.D. et al., "Canadian Laparoscopic Surgery Survey", CJS, vol. 36, No. 3, pp. 217–224, Jun. (1993).

Surgical Endoscopy, "Complications of laparoscopic surgery", pp. 165–166 (1994).

Richard M. Soderstrom, M.D., "Bowel Injury Litigation after Laparoscopy", The Journal of the American Association of Gynecologic Laparoscopists, vol. 1, No. 1, pp. 74–77, Nov. (1993).

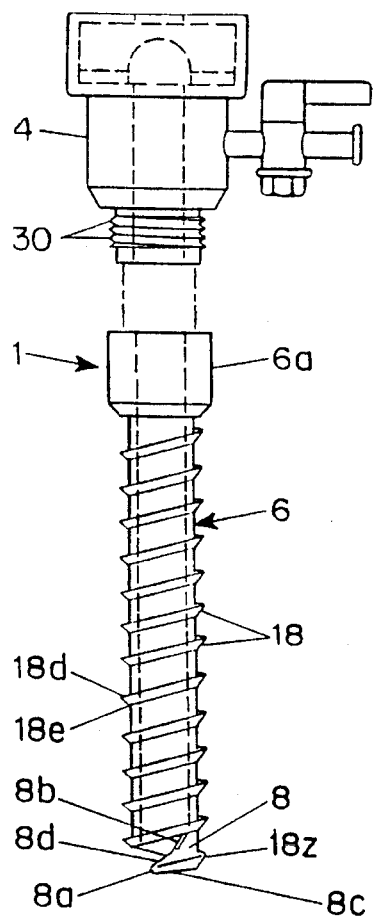
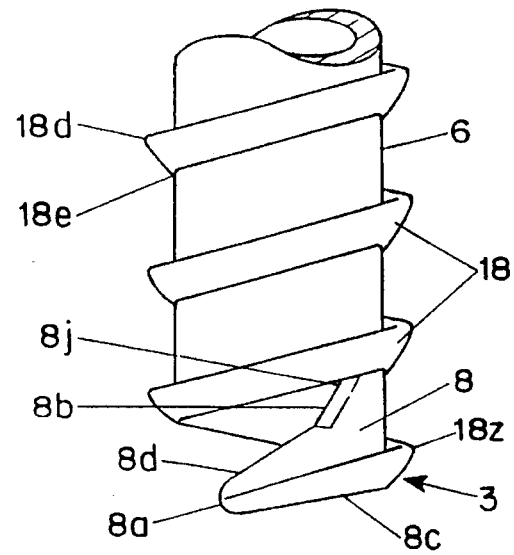
FIG. 8
FIG. 9
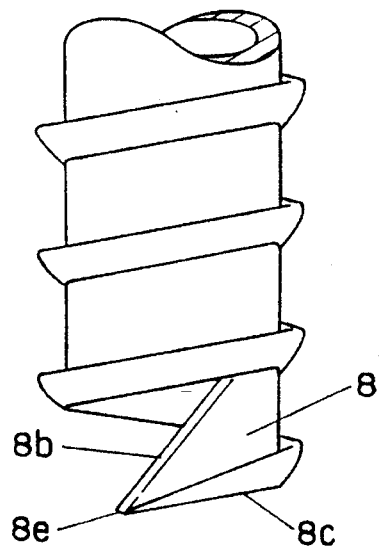
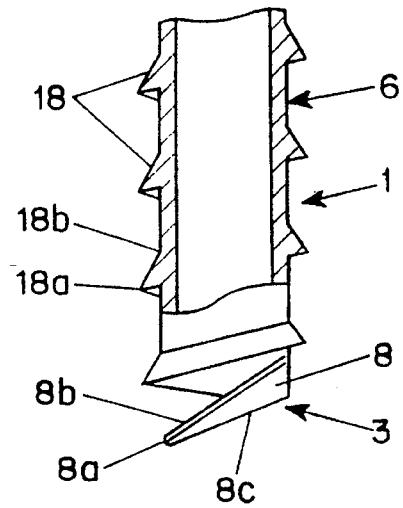
FIG. 10
FIG. 11

5,478,329

TROCARLESS ROTATIONAL ENTRY CANNULA

This invention relates to devices for gaining access to various body cavities for endoscopic procedures, and more particularly to a stabilized trocarless cannula for gaining access to the peritoneal cavity for laparoscopic procedures with or without videoscopy by penetrating a patient's anterior abdominal wall.

BACKGROUND OF THE INVENTION

The surgical procedures of endoscopy, including laparoscopy, with or without videoscopy, are in common use at the present time. The primary advantage of a laparoscopy is that only a small incision is required to access an area where a wide range of surgical procedures can be performed through the small incision with minimal morbidity. Until the present invention, access to the peritoneal cavity during laparoscopy has been gained by the use of a trocar assembly, i.e. a surgical instrument comprising two major components, a trocar (obturator) and a cannula (trocar tube), as described below. The distal end of the cannula of the trocar assembly is blunt and therefore relies on the ability of the trocar to pierce the various layers of the anterior abdominal wall to gain access to the peritoneal cavity. Traditionally, in preparation for a laparoscopy, a small incision corresponding in size to about the diameter of the cannula, is made in the skin and underlying tissues down to and sometimes including an even smaller incision in the anterior fascial sheath sufficient in size to accommodate the tip of the trocar. A Veress needle is then inserted through the incision and underlying tissues into the peritoneal cavity, the peritoneal cavity is insufflated with $CO_2$ gas, and the Veress needle is withdrawn from the peritoneal cavity prior to insertion of the trocar assembly. The distal end of the trocar disposed within the cannula is then placed so that it is in contact with the layers of the body wall exposed by the incision and the trocar is inserted through the tissues. By applying pressure against the proximal end of the trocar, the sharp pointed distal end of the trocar is forced through the different layers of the abdominal wall until it enters the peritoneal cavity carrying the cannula with it. The trocar is then withdrawn, leaving the cannula as an access-way to the peritoneal cavity. Various types of surgical and video instruments are inserted through the cannula into the peritoneal cavity permitting many kinds of surgical procedures to be performed within a patient's abdomen.

There are a number of disadvantages associated with the use of conventional laparoscopic trocars. The principal disadvantages are firstly that significant initial force is usually required to insert the trocar through the layers of the anterior abdominal wall and secondly, that it is a "blind" procedure. The initially applied force may result in the trocar being inadvertently inserted further into the abdominal cavity than is necessary or desirable, and it is not at all unusual in such a situation for the trocar to result in an injury to a major blood vessel or to other visceral organs in the patient's abdomen. These injuries may be of a serious nature, and may even be fatal.

As used below, the term trocar refers to a solid sharp pointed instrument or obturator which is inserted through a trocar tube or cannula, a cannula being a hollow sheath or sleeve, which is capable of receiving surgical instruments, equipment for endoscopic visualization and videoscopy and gas or liquid. The term "distal end" applied to an instrument refers to the end of the instrument that is introduced into the body, and the term "proximal end" refers to the end that remains outside the body during the procedure.

The development and widespread use of trocars for endoscopy has served to focus on the shortcomings and problems to be solved in the design of devices used for accessing body cavities, including the abdominal cavity. Although there have been many modifications and improvements in their design, the problems discussed above have not been overcome. An example of such a modification is a trocar having a retractable sleeve. As soon as the sharp tip of the trocar enters the peritoneal cavity, a spring mechanism should cause the sleeve to snap over the sharp tip of the trocar and in this way prevent injury to any organs that the trocar tip contacts. However, this mechanism may fail. As a result of the force applied to the trocar, the trocar tip pushes the peritoneum ahead of it, and causes forward "tenting" of the peritoneum before and while the tip penetrates the peritoneum. As penetration occurs, the peritoneum surrounding the trocar tip so closely embraces the trocar tip that the passage of the sleeve through the hole in the peritoneum is prevented or delayed. If the sleeve fails to cover the entire tip of the trocar as it penetrates the peritoneum, injuries to intra-abdominal organs by the trocar tip or its sharp beveled edges will not be prevented.

Although trocar assemblies have been modified in various ways, no device has been disclosed using only a cannula, i.e. without a trocar, to gain access to the abdominal cavity. U.S. Pat. No. 5,147,376 discloses a trocar needle having a threaded truncated cone bit having a cutting blade with a rounded edge at its truncated cone end. U.S. Pat. No. 4,191,191 describes an elongated sharp pointed instrument for insertion through an elongated cannula, the sharp pointed instrument having screw threads at its tip, and the proximal portion of the instrument including a crank assembly. U.S. Pat. No. 5,217,441 describes a trocar penetration depth indicator having two threaded sleeves through which a trocar is inserted. U.S. Pat. No. 5,258,003 discloses a trocar which is inserted through a cannula, the trocar having a tapered distal end with screw threads formed on the outer surface of the distal end. The distal end terminates in a flexible tip, through which a hollow needle passes. The needle communicates with a means for indicating changes in pressure as the distal end of the needle enters the peritoneal cavity. U.S. Pat. No. 5,209,736 describes a trocar assembly device including an outer, larger diameter trocar tube and an inner, smaller diameter trocar tube, which extends distally beyond a distal end portion of the outer trocar tube. The distal end of the inner smaller trocar tube is tapered, the tapered end bearing threads on its outer surface to facilitate insertion of the trocar through the layers of the body.

In the above-mentioned patents and in currently used instruments, the trocar or the instrument within the cannula pierces or cuts the body layers and gains access to the peritoneal cavity. Furthermore, the progress of the trocar is achieved as a result of a force that is applied to the proximal end of the trocar, the force being applied substantially perpendicular to the skin surface through which the trocar passes, and the cannula is introduced with the trocar through the hole created by the trocar. The pointed trocar is one of the principal causes of injuries to abdominal viscera during laparoscopy, as described above.

The principal object of the present invention is to provide a safe, easy-to-use, easy-to-maintain and inexpensive apparatus for, and method of, gaining access to body cavities for endoscopic procedures which avoids the above-described disadvantages presented by currently known devices.

Another object of the invention is to provide a cannula for the purpose of accessing the peritoneal cavity, wherein the distal end of the cannula comprises a means for cutting and penetrating the layers of the body wall to gain entry into the peritoneal cavity, without the need for a trocar.

A further object of the invention is to provide a method for inserting the cannula through the abdominal wall and into the peritoneal cavity whereby the progress of the cannula occurs via rotational movement through the layers of the body wall including the peritoneum, rather than by a force applied at substantially 90° to the body wall. This rotational entry of the cannula substantially lessens the potential for damage to the tissues and organs during endoscopy.

The present invention has advantages relating to environmental issues, more specifically to the disposal of used and contaminated cannulae and the cost thereof. Disposal of a cannula made from environmentally friendly, biodegradable materials is simple and inexpensive. Furthermore, the reusable form of the cannula or a portion thereof is safe for use after sterilization, and decreases the enormous number of used contaminated instruments which must be disposed of.

SUMMARY OF THE INVENTION

According to the present invention, there is provided a cannula which has a lumen extending throughout its length and screw threads on its outer surface. The cannula has a distal end and a proximal end, the distal end comprising means for perforating, cutting and penetrating layers of the body wall to gain access to a body cavity without the use of a trocar. The invention is also directed to a method for gaining access to a body cavity using a cannula without a trocar, comprising the steps of (a) providing a cannula having an inner lumen extending throughout its entire length, the cannula having a distal end and a proximal end, the distal end comprising means for cutting and penetrating tissue layers of the anterior abdominal wall and allowing the distal end of the cannula to safely access the peritoneal cavity by rotational movement without the use of a trocar or obturator, the penetrating means comprising at least one hook having a tip that may be sharp or blunt, an upper margin and a lower margin, the upper margin being blunt in part and sharp in part, sharp for its entire length or blunt for its entire length, and the lower margin being blunt in part and sharp in part, sharp for its entire length or blunt for its entire length, (b) making a small incision in the skin and the underlying tissues down to the anterior fascia, sufficient in size to allow passage of the cannula, (c) making a smaller incision than in step (b) in the anterior fascia to create a window therein, the window being sufficient in size to accommodate and engage the tip of the hook of the cannula just below the fascia, (d) placing the distal end of the cannula against the tissues exposed by the hole in the anterior fascia, (e) engaging the tissues of step (d) with the tip of the hook and (f) rotating the proximal end of the cannula in the direction in which the point of the hook is pointing so that the cannula stretches the window in the anterior fascia enough to accommodate the body of the cannula while maintaining an airtight seal around the body of the cannula, the body of the cannula passing through the layers of the anterior abdominal wall until the distal end of the cannula is disposed within the peritoneal cavity.

BRIEF DESCRIPTION OF THE DRAWINGS

The object and advantages of the present invention will become more readily apparent upon reference to the following detailed description when considered together with the accompanying drawings, wherein:

FIG. 8 is an exploded elevational view of an embodiment of the cannula in accordance with the invention, wherein the head portion is detachable from the body portion of the cannula.

FIG. 9 is an enlarged view of the distal end of the cannula shown in FIG. 3.

FIGS. 10–30 are enlarged views of the distal end of alternative embodiments of the cannula in accordance with the invention.

Where appropriate, like elements in the figures have been numbered with like reference numerals.

DETAILED DESCRIPTION OF THE INVENTION

The present invention solves the long-felt problems and fulfills the attendant needs existing in the field of the invention as discussed above.

Figure 1:
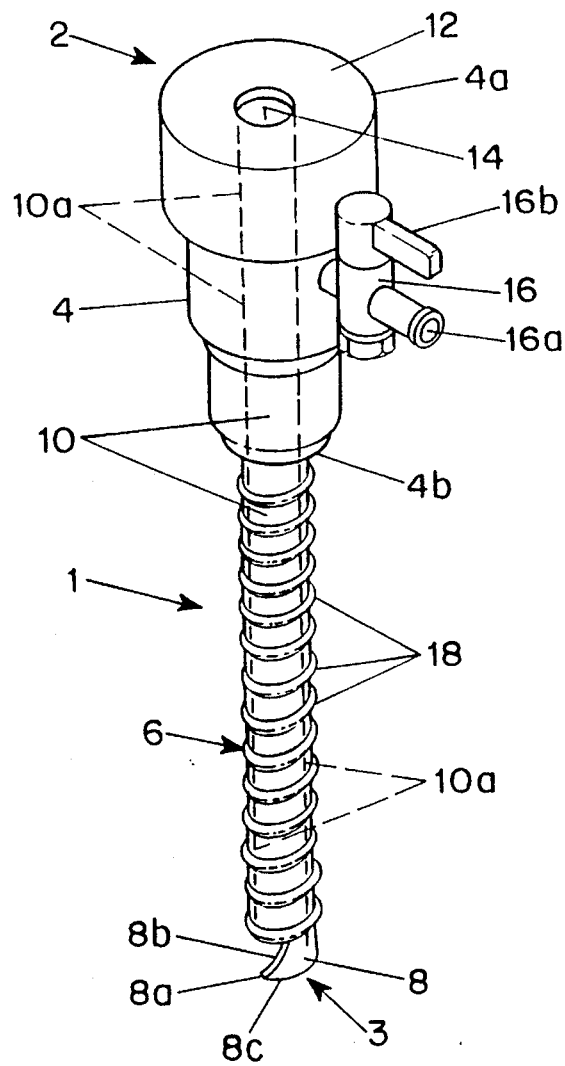
FIG. 1 is a perspective view of a cannula with a head portion, in accordance with the invention.

The present invention is directed to devices for gaining access to body cavities, i.e. for endoscopy with or without videoscopy. The invention will be described with reference to FIGS. 1–36. FIG. 1 shows a cannula 1 having a proximal end 2 and a distal end 3. The proximal end 2 of the cannula 1 bears a head portion 4 which is attached to a body portion 6 at point 4b. The body portion 6 terminates at the distal end 3 of the cannula, the distal end 3 bearing means for penetrating and cutting the layers of the anterior abdominal wall to gain access to the peritoneal cavity. A continuous lumen 10 shown by interrupted lines 10a extends throughout the entire length of the cannula 1. The peripheral portion of the upper or free edge 4a of the head portion 4 is covered by a diaphragm 12. The central portion of the diaphragm 12 has an opening 14 through which the lumen 10 of the cannula 1 communicates with the external environment. A gas or fluid inlet valve 16 mounted on the head portion 4 couples a hollow tube 16a to the lumen 10 of the cannula. A gas source (not shown) may be attached to the hollow tube 16a. The valve handle 16b opens and closes the valve 16 to control the flow of gas into and out of the cannula 1. A flap-valve (not shown) or other sealing means to close off the lumen is disposed within the head portion below the diaphragm. The outer surface of the body portion 6 of the cannula 1 is provided with screw threads 18 which have rounded edges, and do not extend all the way down to the distal end 3. The screw threads may be arranged in a helix and may be disposed on the entire outer surface or a portion thereof. The screw threads may have cutting, blunted or rounded edges, may be broader at their bases or their top portions, and facilitate the stretching of the anterior fascial window and spreading of the tissues as the cannula traverses the layers of the body wall.

The terminal portion of the distal end of the cannula bears a hook or a protrusion, the hook or protrusion having a pointed or a rounded tip. The hook or protrusion has a lower free margin, and an upper margin which connects the tip of the hook with the remainder of the cannula. The tip of the hook and/or part or all of the upper margin and/or part or all of the lower margin constitute the means for perforating, cutting and penetrating the layers of the anterior abdominal wall, allowing the distal end of the cannula to enter the peritoneal cavity. The entire upper and/or lower margin may be blunt or sharp; alternatively, only a portion of the upper and/or lower margin may be sharp. Furthermore, the cutting surface of the sharp margin may be beveled, with the bevel facing inwards towards the lumen of the cannula, or outwards i.e. away from the lumen. In FIG. 1, the hook 8 at the distal end 3 has a rounded tip 8a and a sharp upper edge 8b. The lower edge 8c is blunt.

A preferred embodiment comprises a hook having a rounded tip, a blunt lower margin, a sharp cutting edge on the upper portion of the upper margin and a blunt, non-cutting edge on the lower portion of the upper margin i.e. the portion of the upper margin that abuts the rounded tip. The potential for trauma to the tissues is minimal because the rounded tip, blunt lower margin and blunt lower portion of the upper margin have the effect of simply pushing the tissues and organs ahead of the cannula in the peritoneal cavity. The screw threads on the outer surface of the body of the cannula extend to the distal end. The presence of a screw thread at the distal end thickens, and therefore strengthens, the lower margin, including the tip of the hook. The threads have rounded edges which further minimize damage to the tissues. The top of each screw thread is broader than its base. Thus, the screw threads act like flanges in the peritoneal cavity and the abdominal wall, and when traction is applied to the proximal end of the cannula or to the instruments inserted through the cannula, the screw threads help to maintain the position of the cannula and prevent the distal end of the cannula from slipping out of the peritoneal cavity.

In another preferred embodiment, having a hook with a rounded tip and a blunt, non-cutting upper margin, the rounded tip engages the tissues deep to the fascial layer, and by repeated rotation of the cannula, the rounded tip penetrates the inner tissue layers and enters the peritoneal cavity.

Figure 2:
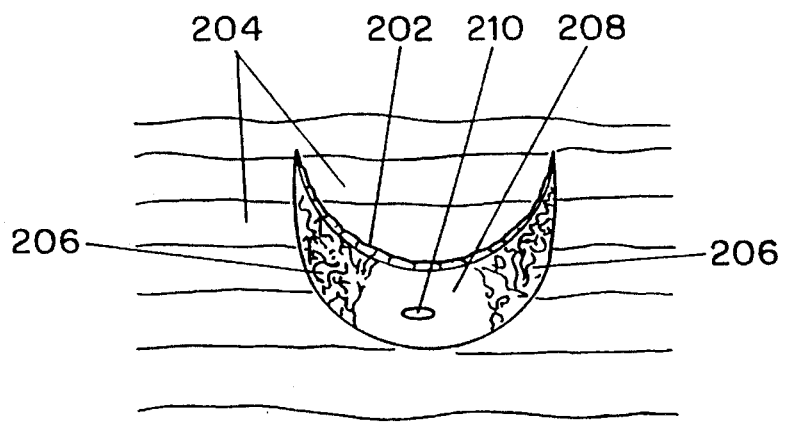
FIG. 2 is a top view of a skin incision and a smaller incision in the anterior fascia below it.
Figure 3:
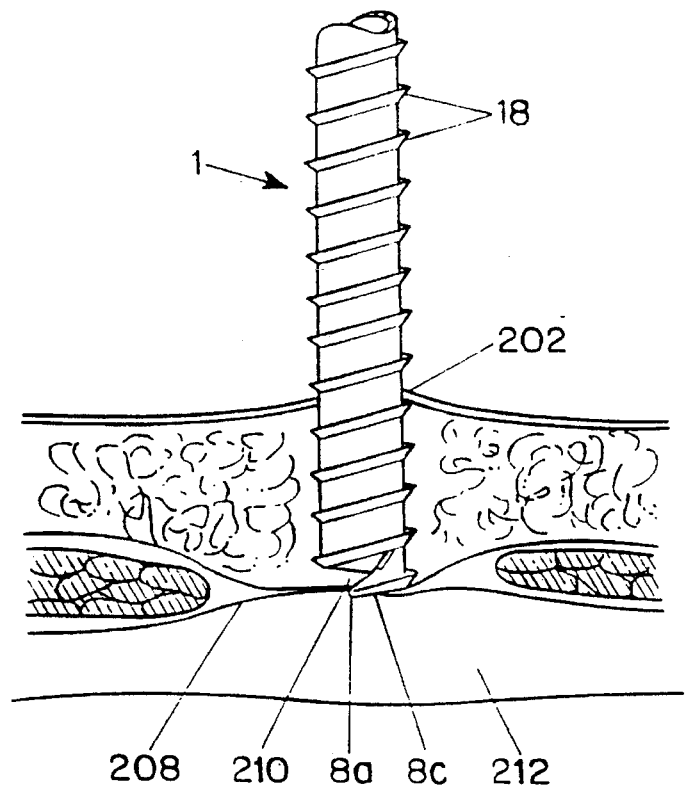
FIG. 3 is a longitudinal cross-sectional view of the anterior abdominal wall showing the distal portion of the cannula prior to its entry into the peritoneal cavity, in accordance with the invention.
Figure 4:
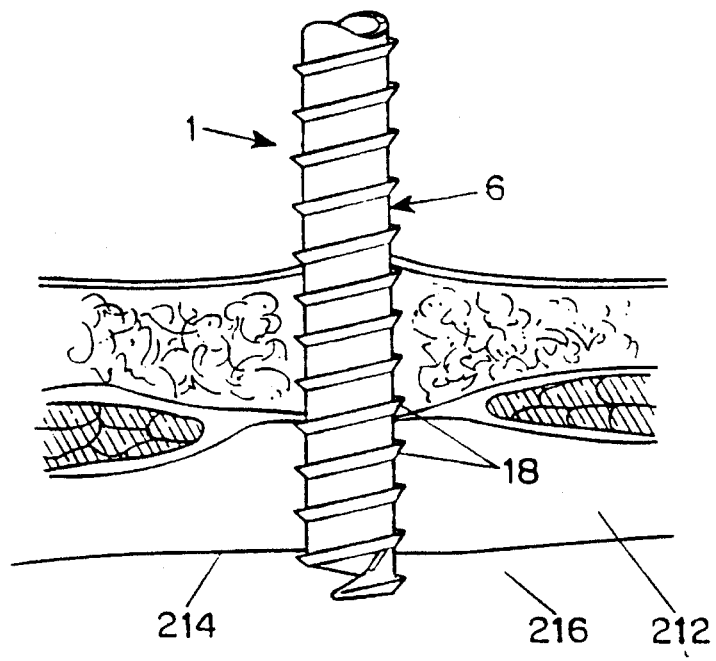
FIG. 4 is a longitudinal cross-sectional view of the anterior abdominal wall showing the distal end of the cannula disposed in the peritoneal cavity, in accordance with the invention.

The method of use of the cannula will be described with reference to FIGS. 2–4. As shown in FIG. 2, a small incision 202 is made in the skin 204 sufficient in size to accommodate the transverse diameter of the cannula not shown. The incision may include the subcutaneous tissues 206 down to the anterior fascia 208; alternatively, the subcutaneous tissues 206 may be separated by blunt dissection. An even smaller incision 210 is then made in the anterior fascia, creating a window sufficient in size to accommodate and engage the tip of the hook of the cannula (not shown) just below the anterior fascia 208. FIG. 3 shows the distal portion of the cannula 1 which has been inserted through the skin incision 202, so that the tip 8a of the hook 8 and lower margin 8c of the cannula contacts the tissues 212 exposed by the hole 210 in the anterior fascia 208, and the tip 8a of the hook 8 engages the tissues 212. FIG. 4 shows the position of the cannula 1 after the proximal end (not shown) of the cannula has been repeatedly rotated, maintaining sufficient pressure on the proximal end of the cannula in the direction in which the tip 8a of the hook 8 is pointing, to allow the penetrating means, the diameter of the cannula 1 and the screw threads 18 to cut and stretch the window or hole 210 in the anterior fascia 208 to accommodate the body 6 of the cannula 1 while maintaining an airtight seal around the body of the cannula. The user continues to rotate the proximal end of the cannula so that the cannula passes through the tissue layers 212 deep to the anterior fascia 208 until the distal end 3 of the cannula 1 is disposed a short distance within the peritoneal cavity 216. The rotational force applied can easily be regulated and controlled by the user to ensure that the force used is just sufficient to allow the distal end to perforate the peritoneum 214 and to enter the peritoneal cavity 216. As described in this paragraph, the cannula is the first instrument to be inserted through the incisions into the peritoneal cavity. Alternatively, the cannula may be inserted only after a Veress needle has been inserted through the incision, the peritoneal cavity has been insufflated with gas via the Veress needle and the Veress needle has been withdrawn therefrom.

Furthermore, while the cannula and method of using it are described with reference to the peritoneal cavity, it should be understood that the apparatus and method of the invention are directed to endoscopic access to any body cavity that can be accessed by such an instrument, for example, but not limited to, the pleural cavity, the pericardial cavity, the extradural cavity, the mediastinum, joint spaces and the retroperitoneal cavity.

It is also possible to insert the laparoscope (attached to a light source) and video monitor into the proximal portion of the cannula, so that as the cannula is advanced through the tissues of the abdominal wall and into the peritoneal cavity, the distal end of the cannula and the tissues ahead of the cannula can be observed by the user through the lumen of the cannula or on the video monitor as the cannula advances. In this way, the cannula is introduced under vision.

There are many embodiments of the invention which will be described with reference to the figures.

Figure 5:
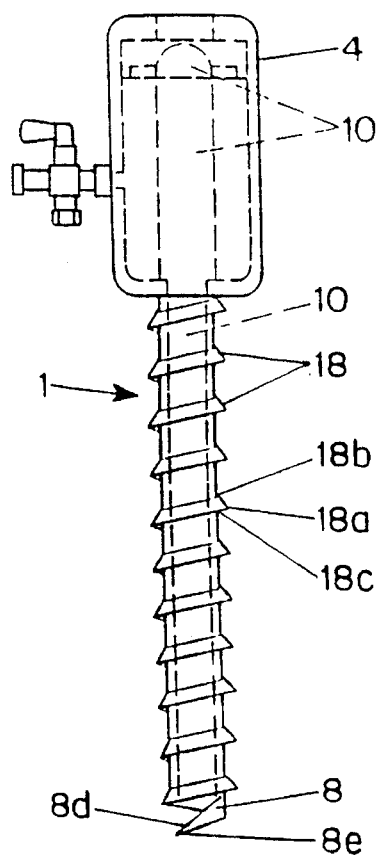
FIG. 5 is an elevational view of another form of a cannula and a longitudinal cross-sectional view of the head portion of the cannula in accordance with the invention.

FIG. 5 shows a cannula 1 having a substantially rectangular-shaped head portion 4. The longitudinal cross-sectional view of the head portion shows the presence of a continuous lumen 10 extending the length of the cannula. The screw threads 18 are wider at their base 18a than at their upper surface 18b, and the screw threads have a sharp cutting edge 18c. The hook 8 at the distal end 3 has a pointed sharp tip 8e and a blunt upper margin 8d.

Figure 6:
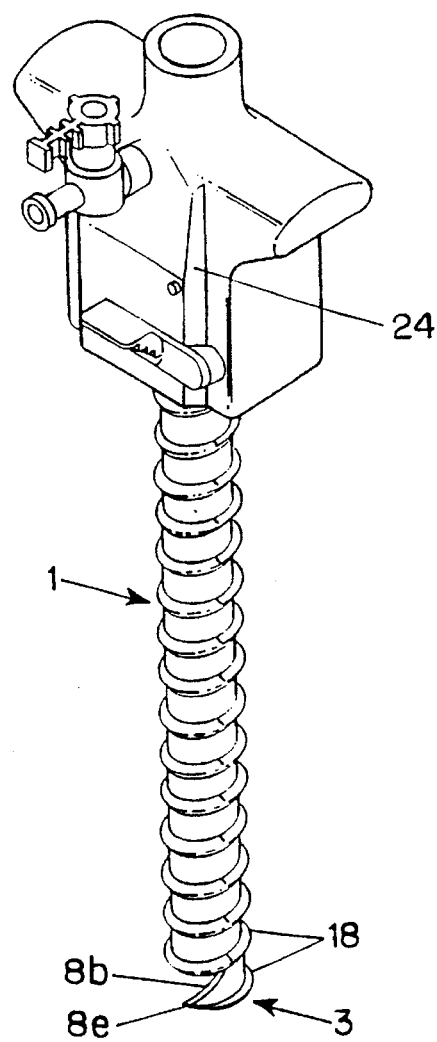
FIG. 6 is a perspective view of a cannula in accordance with the invention.

FIG. 6 shows the lever 24 that opens and closes the flap-valve (not shown) discussed above. Screw threads 18 extend all the way to the distal end 3 of cannula 1. The hook 8 has a pointed sharp tip 8e and a sharp upper edge 8b.

Figure 7:
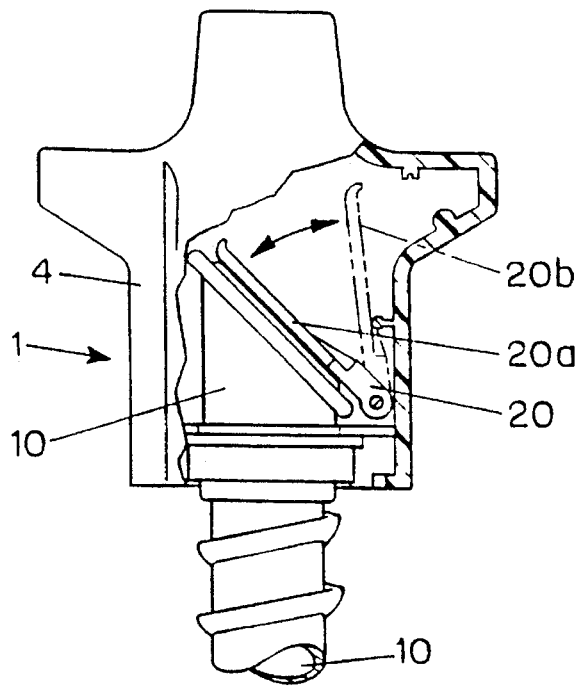
FIG. 7 is a cut, partial sectional view showing the head portion of the cannula.

FIG. 7 shows a flap-valve 20 which, in the closed position, closes off the lumen of the cannula, thereby preventing gas or fluid from escaping from the peritoneal cavity before the introduction of instruments into the lumen 10 of the cannula 1 through the head portion 4 or when instruments are withdrawn therefrom. Further, when the flap-valve 20 is in the closed position 20*a*, the operating room personnel are protected from spray contamination which would otherwise occur by body fluids escaping through the proximal end of the cannula. The flap-valve 20 is shown in the closed position 20*a*, sealing the lumen 10 and in the open position 20*b*, where the lumen communicates with the external environment. When the flap-valve 20 is open, instruments can be inserted into or withdrawn from the cannula 1 and gas can freely escape from the body cavity.

The cannula may be manufactured as a single entity, comprising a head portion and a body portion attached to and integral with the head portion. Alternatively, the body portion may be attached to the head portion by attachable means including, but not limited to, screw-in or clip-on means such that the body portion is detachable from the head portion. The attachable means may allow a head portion to be used with body portions of varying sizes. FIG. 8 shows a cannula 1 which has head and body portions which are detachable from one another. The head portion 4 bears threads 30 which screw into a portion 6*a* of the body portion 6, the portion 6*a* having internal threads (not shown) to receive threads 30.

The cutting and penetrating means at the distal end of the cannula can take various forms, some of which are illustrated in FIGS. 9–30.

FIG. 9 shows the features of the distal portion of the body 6 of the cannula 1 shown in FIG. 8. Screw threads 18 are wider at their upper surface 18*d* than at their base 18*e* and the screw threads 18 extend to the distal end 3, the most distal screw thread 18*z* increasing the thickness of the free lower margin 8*c* of hook 8. The hook 8 has a rounded (blunt) non-traumatic tip 8*a* and the upper margin of the hook 8 has a blunt area 8*d* which abuts the tip of the hook and a sharp area 8*b* disposed on the portion of the hook which is adjacent to the junction 8*j* of the hook and the remainder of the body of the cannula 1. The sharp area 8*b* facilitates enlargement of the anterior fascial window enough to accommodate the cannula's threaded body, while an airtight seal is maintained between the cannula and the tissues.

FIG. 10 shows the features of the perforating, cutting and penetrating means 8 of a cannula 1, wherein the hook 8 has a pointed tip 8*e*, a sharp upper margin 8*b* and a blunt lower margin 8*c*.

FIG. 11 shows the features of the distal portion of the body portion 6 of a cannula 1. The screw threads 18 do not extend to the distal end 3, and the portion of the body 6 towards the distal end 3 of the cannula 1 is thus bare of threads. The screw threads 18 are broader at their base 18*a* than at their upper surface 18*b*.

Figure 12:
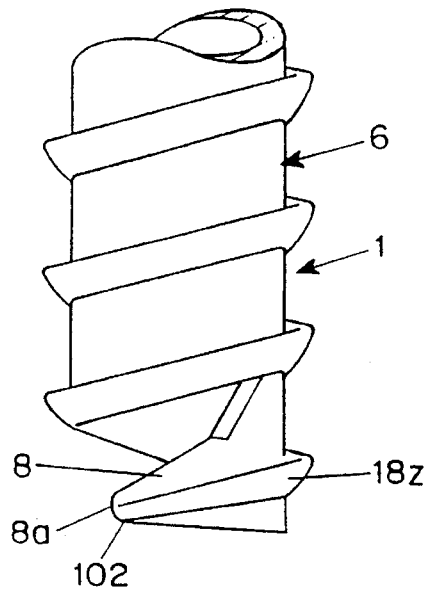

FIG. 12 shows the features of the distal portion of the body portion 6 of a cannula 1, wherein the cannula extends distally beyond the most distal thread, except at the tip 8*a* of the hook 8 where the distal extension of the cannula beyond the most distal thread 18*z* tapers so that it fuses with the tip of the hook 8 at point 102.

Figure 13:
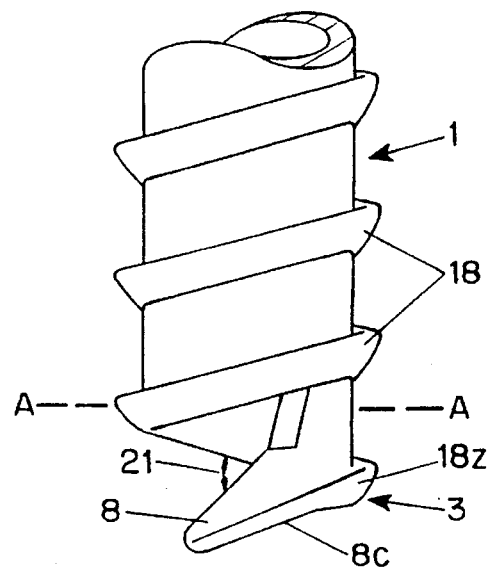

FIG. 13 shows the distal end 3 of a cannula 1 wherein the hook is disposed in a more vertical direction in relation to the axis A—A, thus widening the angle 21. The angle 21 may thus be more obtuse or acute depending on the direction of the hook 8 in relation to the axis A—A. The most distal screw thread 18*z* may follow the direction of the hook, so that it fuses with the hook, increasing the thickness and thus the strength of the lower free margin 8*c* of the hook 8.

Figure 14:
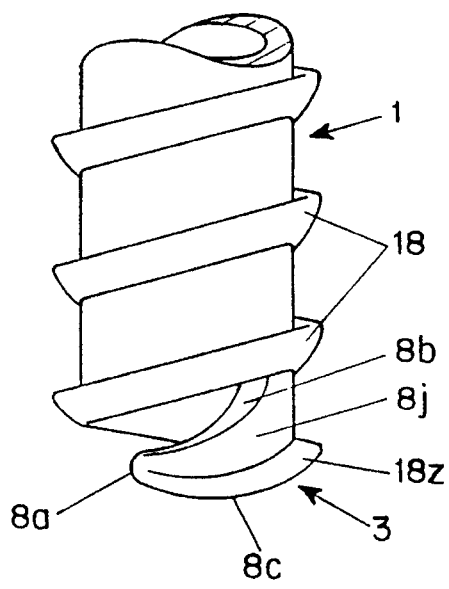

FIG. 14 shows the distal end 3 of a cannula 1 which bears a sickle-shaped hook 8*j*. The screw threads 18 extend to the distal end 3, the most distal screw thread 18*z* being curved so that it is convex at its base, increasing the thickness of the free lower margin 8*c* of the hook 8. The hook 8 has a rounded tip 8*a*, a sharp concave-shaped upper margin 8 and a blunt convex lower margin 8*c*. The upward direction of the tip 8*a* further decreases the potential for injury to tissues.

Figure 15:
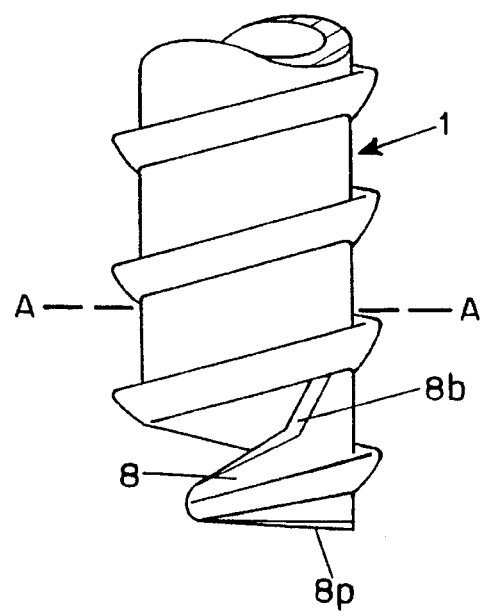

FIG. 15 shows a configuration at the distal end 3 of a cannula 1 which is similar to FIG. 12, except that this embodiment has a double cutting edge, the hook 8 having a sharp lower margin 8*p* which facilitates cutting the tissues that are contacted by the distal end 3 of the cannula 1 and an upper margin 8*b* which is sharp along its entire length, the sharp upper margin 8*b* being angled so that the portion of the upper margin 8*b* adjacent to the tip 8*a* of the hook 8 is less vertical than the remainder of the upper margin 8*b* in relation to the axis A—A.

Figure 16:
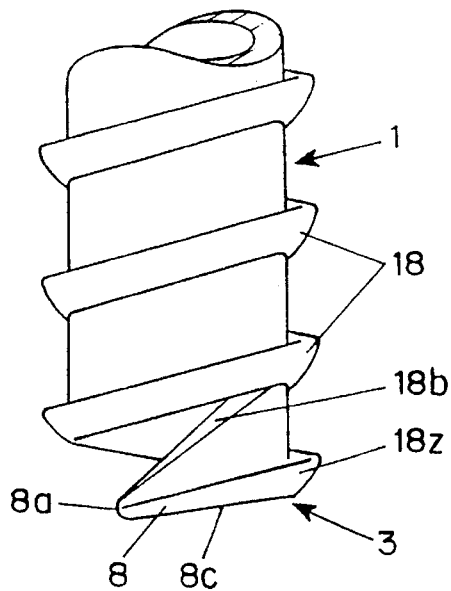

FIG. 16 shows the distal portion of a cannula 1 wherein the screw threads 18 extend to the distal end 3, the most distal screw thread 18*z* increasing the thickness of the free blunt lower margin 8*c* and the tip 8*a* of hook 8. The hook 8 has a sharp upper margin 8*b* and a rounded tip 8*a*.

Figure 17:
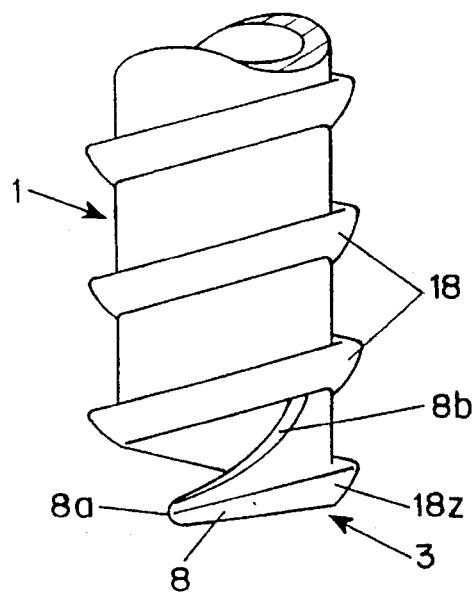

FIG. 17 shows the distal portion of a cannula 1 similar to FIG. 16, except that the sharp upper margin 8*b* of the hook 8 is concave.

Figure 18:
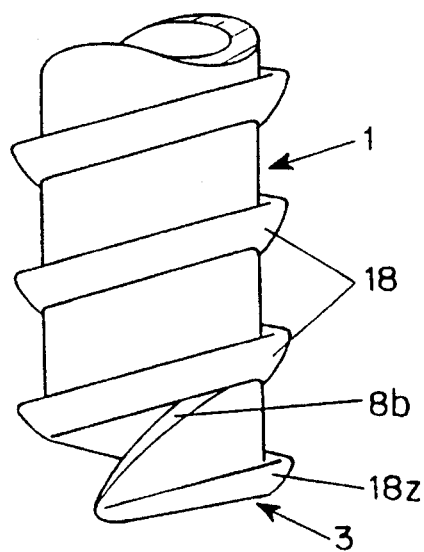

FIG. 18 shows the distal portion of a cannula 1 similar to FIG. 16, except that the sharp upper margin 8*b* of the hook 8 is convex.

Figure 19:
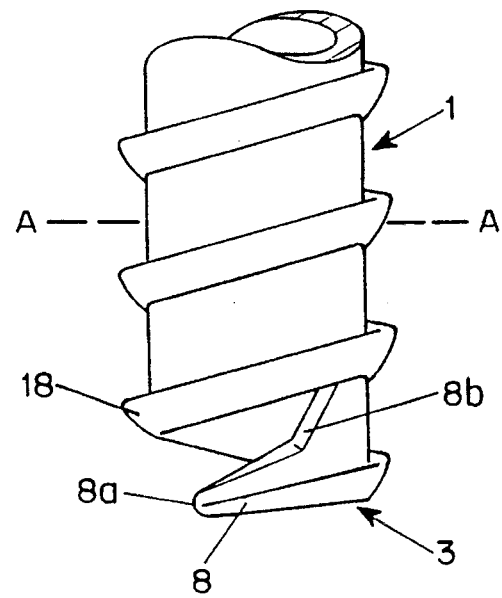

FIG. 19 shows the distal portion of a cannula 1 similar to FIG. 16, except that the upper margin 8*b* of the hook 8 is angled so that the portion of the upper margin 8*b* abutting on the tip 8*a* of the hook 8 is less vertical than the remainder of the upper margin in relation to the axis A—A.

Figure 20:
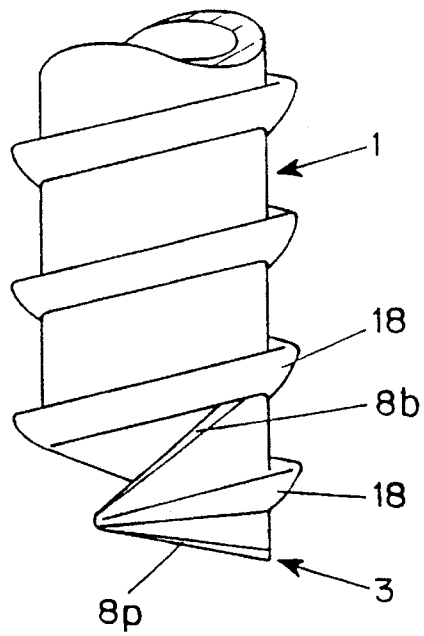

FIG. 20 shows the distal portion of a cannula 1 which has a double cutting edge, the hook 8 having a sharp upper margin 8*b* and a sharp lower margin 8*p*. The screw threads 18 do not extend to the distal end 3 of the cannula.

Figure 21:
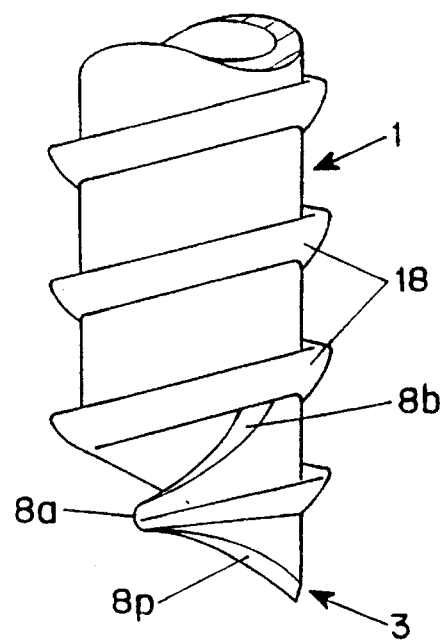

FIG. 21 shows a configuration at the distal end 3 of a cannula 1 which is similar to FIG. 20, except that the upper margin 8*b* and the lower margin 8*p* are concave in shape.

Figure 22:
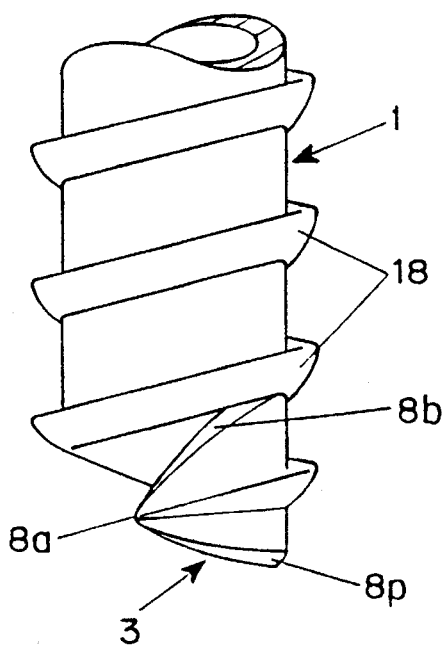

FIG. 22 shows a configuration at the distal end 3 of a cannula 1 which is similar to FIG. 20, except that the upper margin 8*b* and the lower margin 8*p* are convex in shape.

Figure 23:
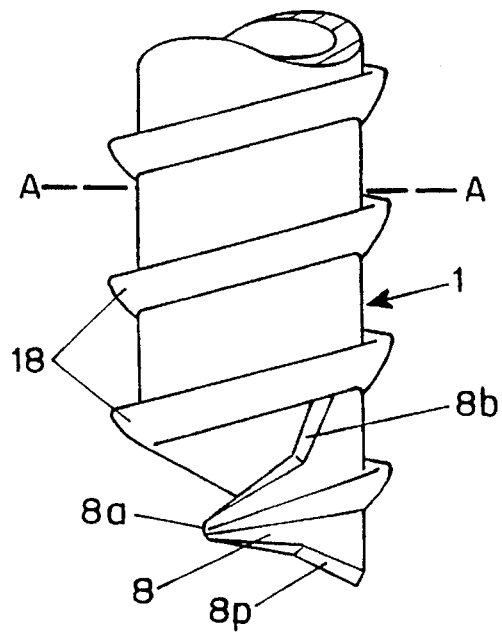

FIG. 23 shows a configuration at the distal end 3 of a cannula 1 which is similar to FIG. 20, except that the upper margin 8*b* and the lower margin 8*p* are angled so that the portions of margins 8*b* and 8*p* abutting on the tip 8*a* of the hook 8 are less vertical than the remainder of the margins 8*b* and 8*p* in relation to the axis A—A.

Figure 24:
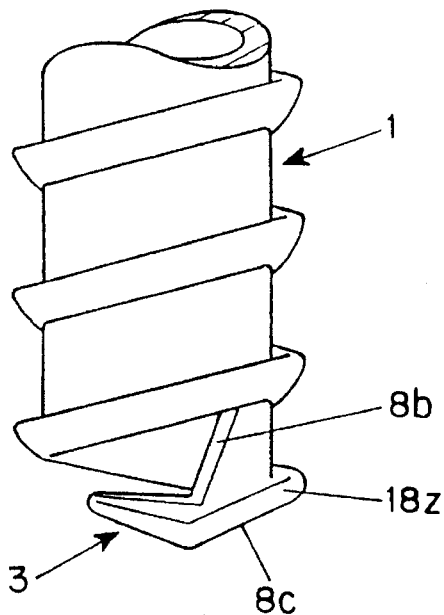

FIG. 24 shows a configuration at the distal end 3 of a cannula 1 which is similar to FIG. 15, except that the most distal thread 18*z* and the lower margin 8*c* follow the same angle as the upper margin 8*b*.

Figure 25:
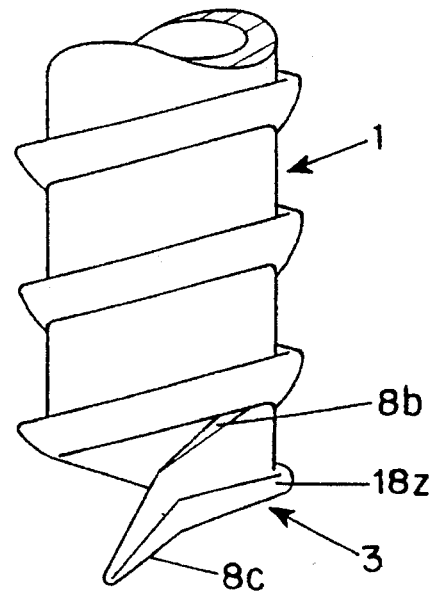

FIG. 25 shows a configuration at the distal end 3 of a cannula 1 which is similar to FIG. 24 except that the upper margin 8*b* of the hook 8, the lower margin 8*c* of the hook 8 and the most distal thread 8*z* are angled in the opposite direction to their counterparts in FIG. 24.

Figure 26:
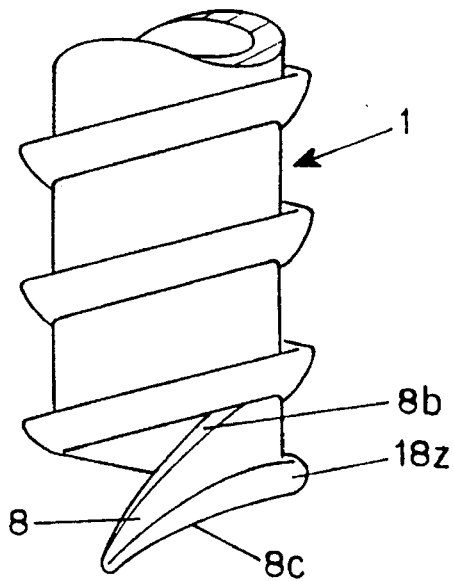

FIG. 26 shows a configuration at the distal end 3 of a cannula 1, wherein the upper sharp margin 8*b* of the hook 8 is convex, the free lower blunt margin 8*c* is concave, and the curve of the most distal thread 18*z* follows the direction of the margins.

Figure 27:
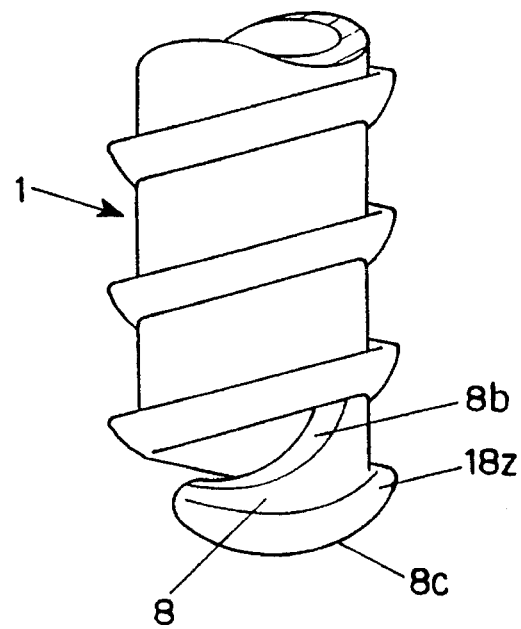

FIG. 27 shows a configuration of the distal end 3 of a cannula 1, wherein the upper sharp margin 8b is concave, the free lower blunt margin 8c is convex, and the curve of the most distal thread 18z follows the direction of the margins.

Figure 28:
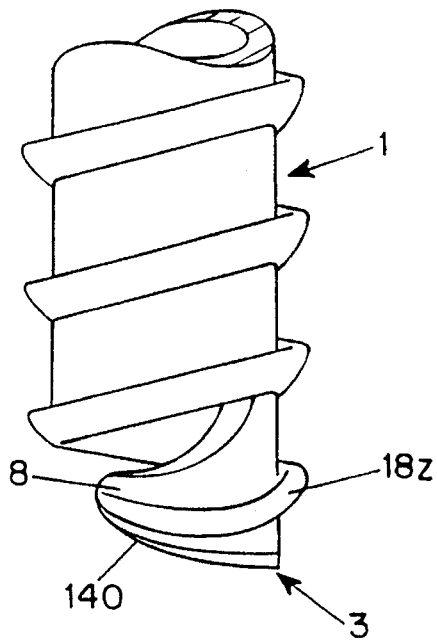

FIG. 28 shows a configuration of the distal end 3 of a cannula 1, which has a hook 8 similar in configuration to the hook shown in FIG. 24, except that the most distal thread 18z does not extend to the distal end 3 of the cannula 1 and the sharp lower margin 140 is formed by the end of the cannula 1 which is distal to the most distal thread 18z.

Figure 29:
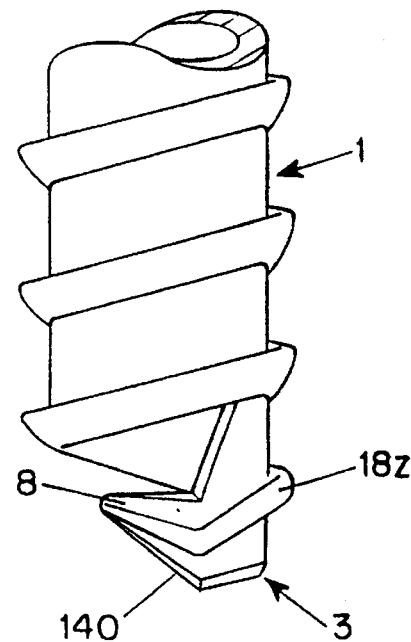

FIG. 29 shows a configuration of the distal end 3 of a cannula 1, which has a hook 8 similar in configuration to the hook 8 in FIG. 24, except that the sharp lower margin 140 is formed by the end 3 of the cannula which is distal to the most distal thread 18z.

Figure 30:
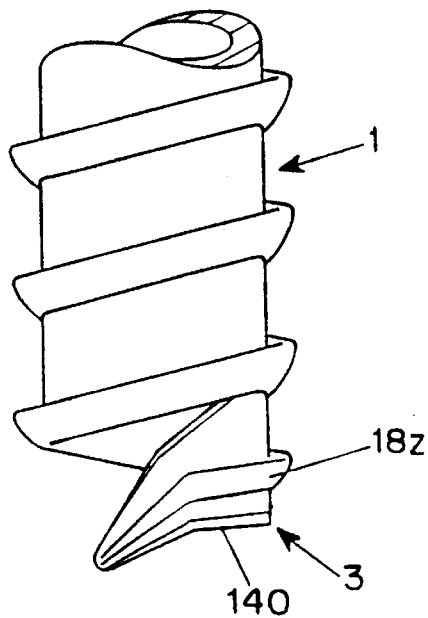

FIG. 30 shows a configuration of the distal end 3 of a cannula 1, which has a hook 8 similar in configuration to the hook 8 in FIG. 25, except that the sharp lower margin 140 is formed by the end 3 of the cannula which is distal to the most distal thread 18z.

Figure 31:
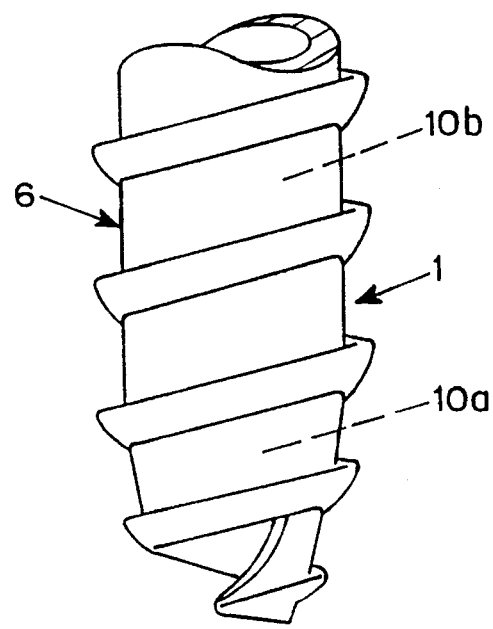
FIG. 31 is a partial elevational view of a cannula in accordance with the invention, having a tapered distal portion.

The cannulae of the present invention have a diameter ranging from about 1 millimeter to about 25 millimeters in diameter, more usually from 5 to 15 millimeters. The lengths and diameters of the cannulae are within ranges known and used for procedures in children and adults. The diameter of the lumen of the cannula may be uniform throughout its length. Alternatively, the cannula may be tapered, so that the distal end of the cannula is narrower than the proximal end. With this variation in diameter, it is understood that means are used to maintain an airtight seal at the proximal end, even where the diameter of an instrument inserted through the cannula is less than the diameter of the proximal end of the cannula. When this tapered cannula is used, the window in the anterior fascia is progressively enlarged by the increasing diameter of the cannula from its distal to its proximal end, and an airtight seal is ensured between the cannula and the tissues through which the cannula passes. FIG. 31 shows the body 6 of a tapered cannula 1, wherein the diameter of the lumen 10a of the distal portion of the body is less than the diameter of the lumen 10b of the more proximal portion of the body.

Figure 32:
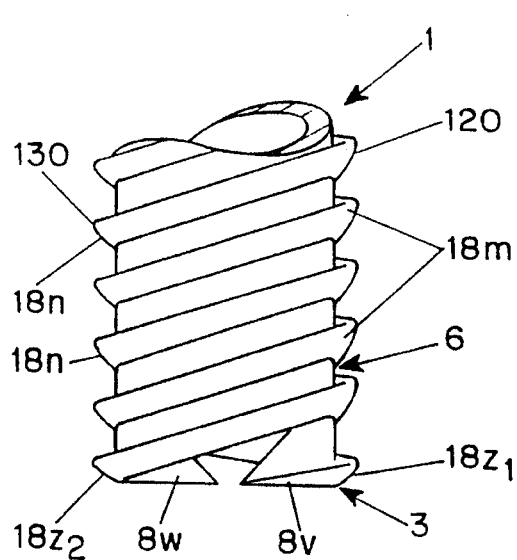
FIG. 32 is an enlarged partial view of the body of a cannula in accordance with the invention, wherein the body of the cannula bears screw threads arranged in two helices.

FIG. 32 shows the distal portion of a cannula 1, wherein the body 6 of the cannula 1 bears screw threads arranged in 2 helices. The first helix 120 and the second helix 130 are in the same plane and parallel to one another. The screw threads 18m of the first helix 120 are disposed between and are parallel to the screw threads 18n of the helix 130. The screw threads 18m of the first helix 120 and the screw threads 18n of the second helix 130 extend to the distal end 3 of the body, the most distal screw thread $18z_1$ of the first helix 120 terminating in hook 8v and the most distal screw thread $18z_2$, of the second helix 130 terminating in hook 8w.

Figure 33:
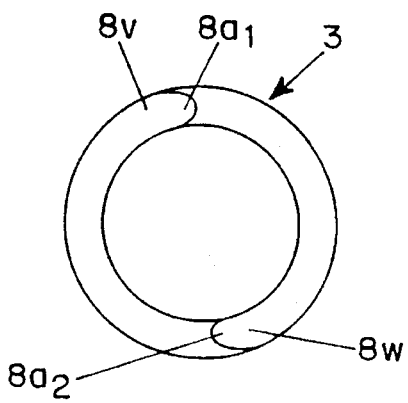
FIGS. 33 and 34 are enlarged end views of alternative forms of the distal end of the cannula shown in FIG. 32.

FIG. 33 shows the distal end of the cannula depicted in FIG. 32 as seen end-on from the distal end 3. Hooks 8v and 8w have rounded tips $8a_1$, and $8a_2$ respectively.

Figure 34:
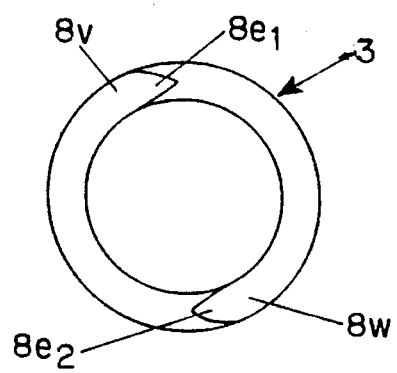

FIG. 34 shows an end-on view of the distal end of a cannula having a similar configuration to the cannula depicted in FIG. 32, except that the hooks 8v and 8w have pointed tips $8e_1$, and $8e_2$ respectively.

Figure 35:
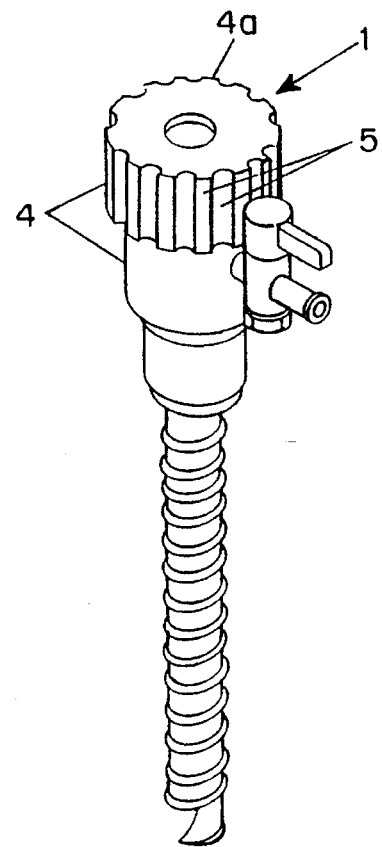
FIG. 35 is an elevational view of a cannula, with a serrated head portion, in accordance with the invention.

FIG. 35 shows a cannula 1 of the invention, wherein the most proximal portion of the head 4, i.e. the portion of the head adjacent to and including the upper or free edge 4a of the head portion 4, has a serrated outer surface 5 which enables the user to grasp the head firmly while rotating the cannula 1. The entire head portion or any portion thereof may have a serrated surface. The presence of a serrated portion prevents the head portion from slipping from the user's grasp, as may occur when using a cannula which has a head portion with a smooth outer surface.

Figure 36:
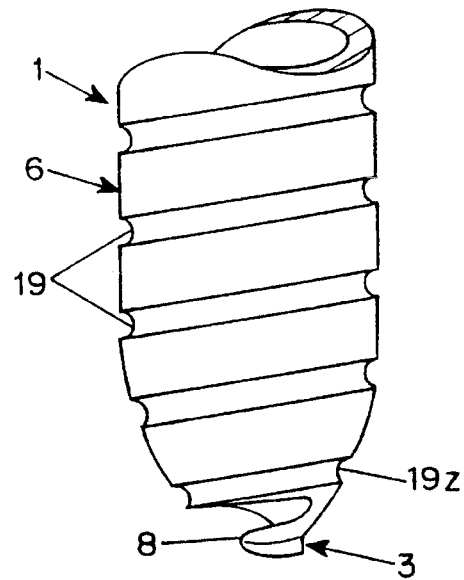
FIG. 36 is an enlarged partial view of the body of a tapered cannula in accordance with the invention, wherein the body of the cannula bears grooves on its outer surface.

FIG. 36 shows a portion of the body 6 of a cannula 1, wherein the outer surface of the body 6 has grooves or depressions 19 instead of screw threads as described above. If the anterior fascia should slip into a groove or depression, an airtight seal is maintained, as the anterior fascia recoils slightly from its prior position due to its inherent slight elasticity.

The cannulae of the invention may be made from any of the materials used in the field including, but not limited to, teflon, natural rubber, synthetic rubber, plastics and thermoplastics including, but not limited to, polyvinylchloride, polyethylene, polyurethane or the like, or metals including, but not limited to, aluminum or stainless steel. The materials used may be rigid or flexible. Thus, the entire cannula may be rigid or flexible. Alternatively, the cannula may comprise a rigid portion and a flexible portion, for example, but not limited to, a rigid head portion and a flexible body portion or flexible head and body portions and rigid screw threads. The tube may be made from any inert materials used in this field, and the materials used may be opaque or clear. The cannula may be radiopaque or radiolucent. Alternatively, a radiolucent cannula may have a radiopaque tip. Any or all of the screw threads, or any parts thereof, may be radiopaque.

The cannulae of the invention may be disposable or reusable. In the embodiments of the invention having a body and a head which are detachable, an example of which is shown in FIG. 5, the head portion may be reusable and the body portion disposable, or vice-versa. Alternatively both portions may be reusable or disposable. Furthermore, the body of the cannula may be rigid. Alternatively, the body of the cannula or a portion thereof may be flexible. Because the head portion of the cannula is expensive to manufacture, the most economical embodiment comprises a reusable head portion which can be attached to several sizes of disposable body portions.

Cannulae presently in use may be modified in accordance with the present invention. For example, the cannula of the present invention could replace the Veress needle and its cannula, thus avoiding possible trauma produced by the Veress needle. Furthermore, cannulae in accordance with the present invention can be compatible with or adapted to other instruments disclosed for video laparoscopic and/or other endoscopic procedures. For example, the cannula of the invention can have gradation marks on its outer surface to indicate the depth of the distal end of the cannula from the surface of the body. Furthermore, the outer surface of the cannula may bear projections which prevent the cannula from being inserted into the body cavity beyond the desired depth.

The description of the above embodiments is meant to be illustrative of the scope and spirit of the invention. These embodiments will make apparent other embodiments and examples which are within contemplation of this invention.

I claim:

1. A cannula for accessing a body cavity said cannula having a distal end and a proximal end, a lumen within the cannula extending throughout its entire length, the distal end comprising means for penetrating tissue layers of a body wall to access the body cavity, wherein said lumen is sufficiently large throughout its length to allow passage of instruments directly into the body cavity and wherein said penetrating means is peripherally situated.

2. A cannula according to claim 1 wherein the cannula includes a head portion at its proximal end and a body portion attached to and extending from the head portion to the distal end of the cannula, the head portion comprising an inlet for gas and a valve means, the valve means preventing escape of gas and fluid from the body.

3. The cannula according to claim 2 wherein the body portion of the cannula tapers from a point along its length to the distal end of the cannula, whereby the diameters of the body portion of the cannula and its lumen are smaller at its distal end than at said point.

4. A cannula according to claim 2, wherein the body portion of the cannula has at least one screw thread around its outer surface.

5. A cannula according to claim 4 wherein the body portion of the cannula has a first and second helix of screw threads around its outer surface, the screw threads of the second helix being disposed between the screw threads of the second helix, the screw thread of each helix terminating in a hook at the distal end of the cannula.

6. A cannula according to claim 2, wherein the head portion and body portion are attached by means whereby they can be detached from and re-attached to one another.

7. A cannula according to claim 6, wherein the head portion is attached to the body portion by screw-on means.

8. A cannula according to claim 6, wherein the head portion is attached to the body portion by clip-on means.

9. A cannula according to claim 6, wherein the head portion is disposable and the body portion is reusable.

10. A cannula according to claim 6, wherein the head portion is re-usable and the body portion is disposable.

11. A cannula according to claim 2 or claim 10, wherein the head portion and body portion are re-usable.

12. A cannula according to claim 2 or claim 10, wherein the head portion and body portion are disposable.

13. A cannula according to claim 1, wherein the body cavity is the peritoneal cavity.

14. A cannula according to claim 1, wherein the penetrating means at the distal end comprises at least one hook having a sharp tip.

15. A cannula according to claim 1, wherein the penetrating means at the distal end comprises at least one hook having a rounded tip.

16. A cannula according to claim 1, wherein the penetrating means at the distal end comprises a hook having a sharp upper margin.

17. A cannula according to claims 1, wherein the hook at the distal end has a sharp tip and at least one cutting edge.

18. A cannula according to claim 1, wherein the penetrating means comprises a hook having a tip, an upper margin and a lower margin in a combination selected from a group consisting of a sharp or blunt tip, an upper margin that may be blunt in part and sharp in part, sharp for its entire length or blunt for its entire length and a lower margin that may be blunt in part and sharp in part, sharp for its entire length or blunt for its entire length.

19. A cannula according to claim 1, wherein the lumen has a uniform diameter throughout its length.

20. A cannula for accessing a body cavity via a small incision through tissue layers of the abdominal wall, the incision at least through the anterior fascial layer being substantially smaller than a transverse dimension of the cannula, the cannula comprising a distal end and a proximal end;

a lumen extending throughout the entire length of the cannula;

means at the distal end of the cannula to permit the cannula to access the body cavity; and means on the cannula to facilitate spreading of the tissues around the incision, wherein said lumen is sufficiently large throughout its length to allow passage of instruments directly into the body cavity and wherein the access means at the distal end of the cannula is peripherally situated.

* * * * *

UNITED STATES PATENT AND TRADEMARK OFFICE
CERTIFICATE OF CORRECTION

PATENT NO. : 5,478,329
DATED : December 26, 1995
INVENTOR(S) : Artin M. Ternamian It is certified that error appears in the above-indentified patent and that said Letters Patent is hereby corrected as shown below:

On the title page:

Item [56]: 1st col., 3rd from bottom line, "D." should read -- Dr. --;

Col. 11, line 29, "claim 10" should read -- claim 6 --;

line 31, "claim 10" should read -- claim 6 --.

Signed and Sealed this

Thirty-first Day of December, 1996

Attest:

BRUCE LEHMAN

Attesting Officer      Commissioner of Patents and Trademarks